(12) United States Patent
Sharp

(10) Patent No.: US 6,565,541 B2
(45) Date of Patent: May 20, 2003

(54) CANNULA GUARD AND CANNULA FOR A SYRINGE

(75) Inventor: Fraser R. Sharp, Vancouver (CA)

(73) Assignee: Inviro Medical Devices Ltd., Bridgetown (BB)

(*) Notice: Subject to any disclaimer, the term of this patent is extended or adjusted under 35 U.S.C. 154(b) by 0 days.

(21) Appl. No.: 09/905,671

(22) Filed: Jul. 18, 2001

(65) Prior Publication Data

US 2003/0018303 A1 Jan. 23, 2003

(51) Int. Cl.[7] .................................................. A61M 5/32
(52) U.S. Cl. ........................................ 604/192; 604/240
(58) Field of Search ............................... 604/93.01, 192, 604/263, 240, 241, 264, 272, 905; 206/365

(56) References Cited

U.S. PATENT DOCUMENTS

| | | | | |
|---|---|---|---|---|
| 4,740,205 A | * | 4/1988 | Seltzer et al. ............... | 604/192 |
| 5,147,325 A | * | 9/1992 | Mitchell et al. ............. | 604/192 |
| 5,190,529 A | * | 3/1993 | McCrory et al. ............ | 604/175 |
| 5,250,037 A | * | 10/1993 | Bitdinger ...................... | 604/192 |
| 5,360,404 A | | 11/1994 | Novacek et al. | |
| 6,213,978 B1 | * | 4/2001 | Voyten ................... | 604/164.01 |

* cited by examiner

Primary Examiner—Teresa Walberg
Assistant Examiner—Thor Campbell
(74) Attorney, Agent, or Firm—Nixon & Vanderhye

(57) ABSTRACT

A plastic cannula has a hub mounting a pair of flanges forming a Luer lock connection with a standard syringe having female threads about its distal end. A cannula guard receives the cannula and has radially inward projections for engaging portions of the cannula to rotate the cannula guard and cannula relative to the syringe to fix the cannula onto the syringe. The cannula guard is removed by rotating the guard in an opposite direction, causing projections along the inner surface of the cannula guard to ratchet past ribs on the cannula, enabling removal of the cannula guard from the cannula without applying sufficient torque to the cannula to remove the cannula from the syringe.

8 Claims, 6 Drawing Sheets

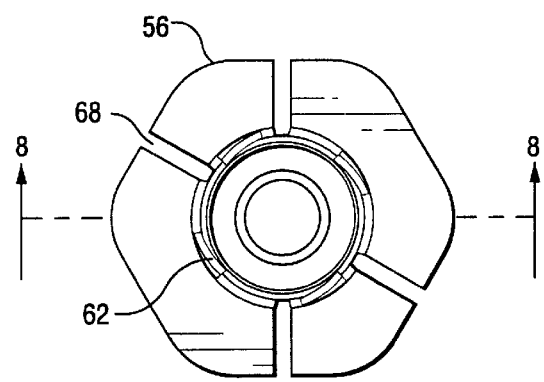
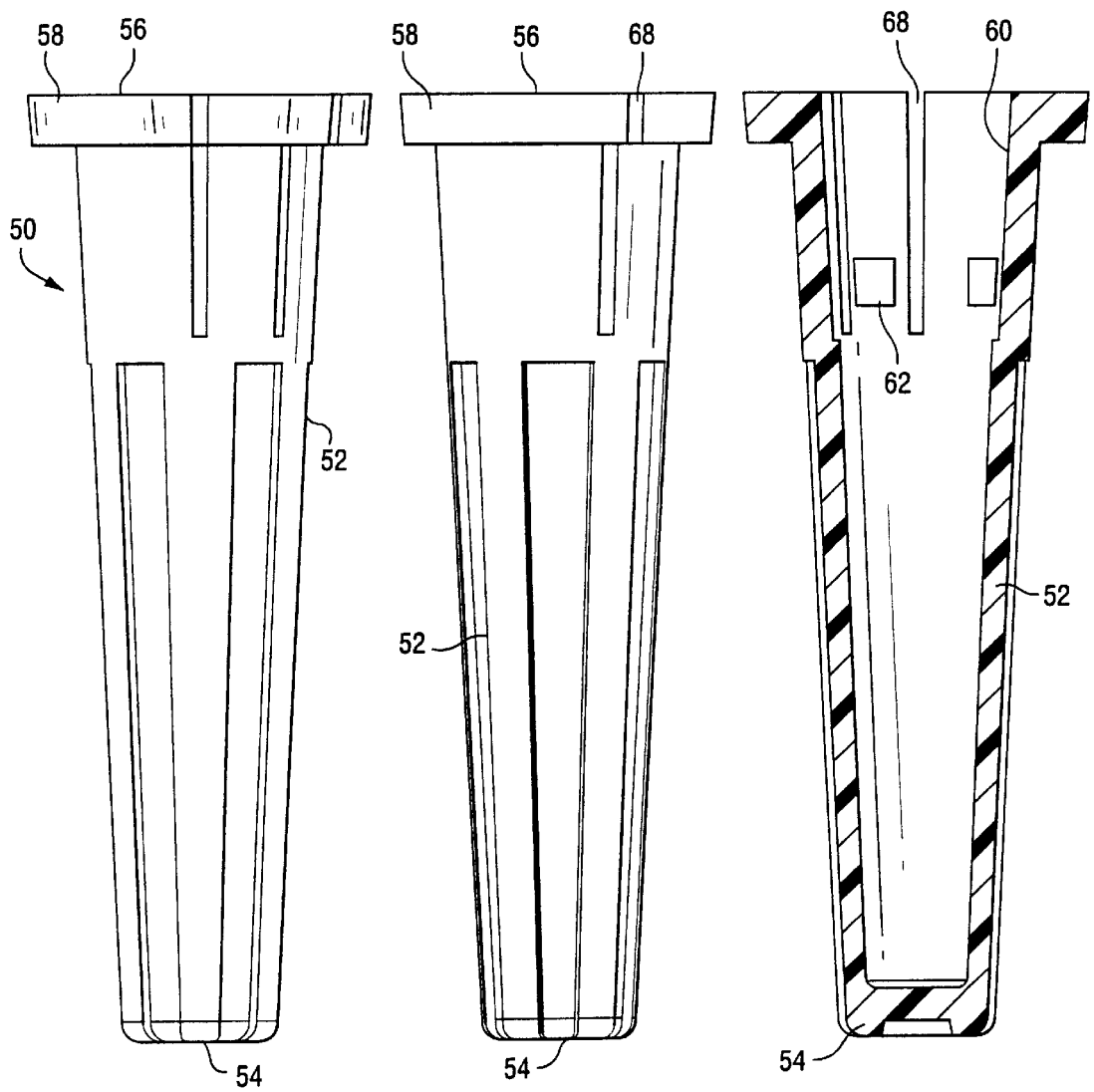
Fig. 5
Fig. 6   Fig. 7   Fig. 8

CANNULA GUARD AND CANNULA FOR A SYRINGE

TECHNICAL FIELD

The present invention relates to a cannula guard and a cannula for use in the medical field and particularly relates to a cannula for penetrating membranes or septums as commonly used in medication vials, intravenous bags, access ports and the like, and a cannula guard protecting the cannula and preventing removal of the cannula from the syringe using the cannula guard, thereby preventing attachment of a standard Luer metal needle to the syringe.

BACKGROUND

Syringes used in the medical field typically have a metal needle mounted at the front end of the barrel, allowing for aspiration of fluid into the syringe and subsequent injection of the fluid into the patient through the skin or indirectly through a previously placed intravenous infusion line. Access to those lines are provided by a variety of devices called access ports. Those access ports typically include a septum or membrane and which may be pre-slit to allow access by a blunt, usually plastic, cannula. In assignee's prior application Ser. No. 590,681, there is provided a blunt cannula which is useful for penetrating both pre-slit septums or puncturing non-pre-slit septums. The cannula of that application is sufficiently sharp to allow such penetration but insufficiently sharp to accidentally or easily puncture a healthcare worker's skin or a rubber glove protecting the healthcare worker's hand. The cannula of that prior application is particularly constructed for use in conjunction with or integral to an adapter in the syringe barrel whereby the adapter, as well as the cannula, can be pulled back into the barrel of the syringe after use, precluding re-exposure of the cannula or reuse of the syringe. That is, the cannula is particularly useful with a retractable needle safety syringe in which the cannula can be retracted into the barrel subsequent to use.

Safety-type syringes have been mandated for use by law in all states of the United States in most clinical situations. These safety-type syringes may have various configurations. For example, the needle may be withdrawn into the barrel subsequent to use. Alternatively, a sheath may be projected over the projecting tip of the needle, protecting against needlestick injuries. Various other types of safety syringes have been proposed. It will be appreciated that the safety syringes per se and the legislation mandating their use constitute efforts to avoid needlestick injuries which are of growing health concern because of the potential for disease transmissions such as HIV or Hepatitis B and C.

While the plastic cannula of the above-identified prior application is insufficiently sharp to easily penetrate a healthcare worker's skin, and consequently may be used in conjunction with a standard syringe without safety features, it is of prime importance that the cannula cannot be removed from the syringe and replaced by a standard metal needle. This would result in a non-safety or standard syringe and needle and its use may be contrary to those statutes which mandate use of safety syringes. The cannula set forth in the above-identified prior patent application, of common assignee herewith, is particularly useful in conjunction with the retractable syringe whereby the cannula is withdrawn into the barrel subsequent to use. However, where the cannula is used with a standard syringe, there remains the possibility of removing the cannula from the syringe and replacing it with a standard needle whereby the syringe becomes a non-safety syringe. It will be appreciated that a standard needle assembly comprises a needle hub and a steel needle secured to the hub. A standard Luer fit or Luer lock is used to secure the needle to the syringe. In a Luer lock, the needle is secured to the syringe by threading the flanges of the needle hub along a partially female threaded projection on the syringe barrel or other part. Alternatively, in a Luer fit, the needle hub may be frictionally engaged with a tapering projection on the barrel end which does not have any positive securement to the barrel except for the friction-fit. Most healthcare workers reflexively rotate the needle when applying the needle to the syringe because of the common usage of the Luer lock as a method of connecting the needle to the syringe barrel. Also, a needle guard is typically employed overlying the needle and part of the hub prior to needle usage and the guard facilitates the grasping and rotation of the needle to apply the needle to the syringe end to remove a needle if it is desired to attach another needle after filling the syringe to administer the injection.

The plastic cannula has a similar standard connection, i.e., Luer lock or Luer fit, with a standard syringe. Thus, when applying the cannula to the standard syringe, the healthcare worker reflexively rotates the cannula and a needle guard in part surrounding the cannula to apply the cannula to the syringe. By design, the needle guard may have features which inhibit or prevent the removal of the plastic needle after it has been attached.

DISCLOSURE OF THE INVENTION

In accordance with the present invention, the needle guard and plastic cannula are constructed with cooperable surfaces such that a torque applied to the cannula guard is transmitted to the cannula in a direction normally applying the cannula to the syringe barrel. For example, using a Luer lock, the cannula guard engages and rotates the cannula in a direction such that the flanges of the cannula are screwthreaded into the female threads on the barrel end. The cannula guard and cannula, however, also have cooperable surfaces which, upon rotation of the cannula guard in an opposite direction, causes the guard to slip relative to the cannula, disabling the cannula from rotation in a direction unthreading the cannula from the barrel end. Thus, a torque applied to the cannula guard in a direction opposite to the direction securing the cannula to the standard needle barrel results generally in a ratcheting action, precluding removal of the cannula from the syringe. In this manner, the cannula cannot easily, if at all, be removed from the syringe by use of the cannula guard and, hence, a standard metal needle cannot be applied to the syringe with the syringe being reused without safety syringe features. While it may be possible to manually unthread the cannula without the use of any type of guard from the syringe barrel, healthcare workers typically would not grasp and rotate the cannula per se to remove it from the syringe and replace it with a needle as this would be contrary to conventional training and practice.

In a preferred embodiment according to the present invention, there is provided apparatus for releasably securing a cannula to an end portion of a syringe comprising a cannula body having an elongated cannula portion projecting from the hub terminating in a cannula tip, the body being formed of a plastic material and having a passage therethrough for transmission of a fluid, the cannula hub having a surface for engaging the end portion of the syringe and a cannula guard including a sleeve closed at one end and open at its opposite end for receiving the elongated cannula portion and a portion of the cannula hub within the sleeve, the cannula guard and the cannula having cooperable surfaces, respectively, configured to transmit a torque applied to the cannula guard in a first direction to the cannula to engage the cannula and syringe end portion thereby to secure the cannula and syringe to one another and to enable relative rotation of the cannula guard and the cannula without transmission of substantial torque from the cannula guard to the cannula when a torque is applied to the cannula guard in a second direction opposite the first direction.

BRIEF DESCRIPTION OF THE DRAWINGS

FIG. 5 is a top plan view thereof;

FIGS. 6 and 7 are side elevational views of the cannula guard with FIG. 7 being rotated relative to the cannula guard of FIG. 6;

FIG. 8 is a cross-sectional view taken generally about on line 8—8 in FIG. 5;

BEST MODE FOR CARRYING OUT THE INVENTION

Figure 1:
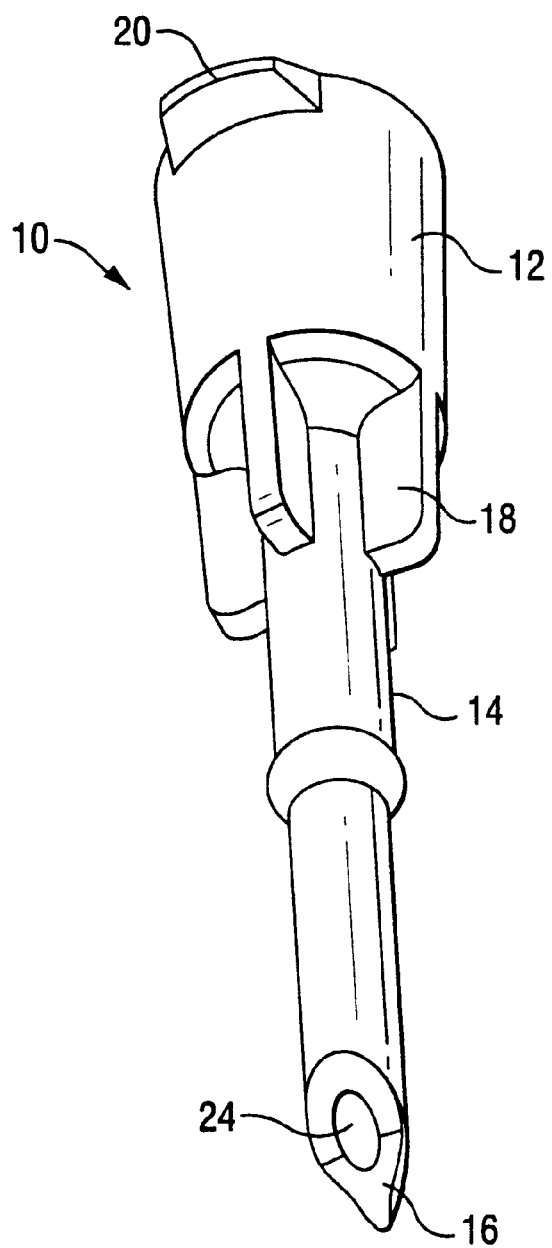
FIG. 1 is a perspective view of a cannula for use in the present invention.
Figure 2:
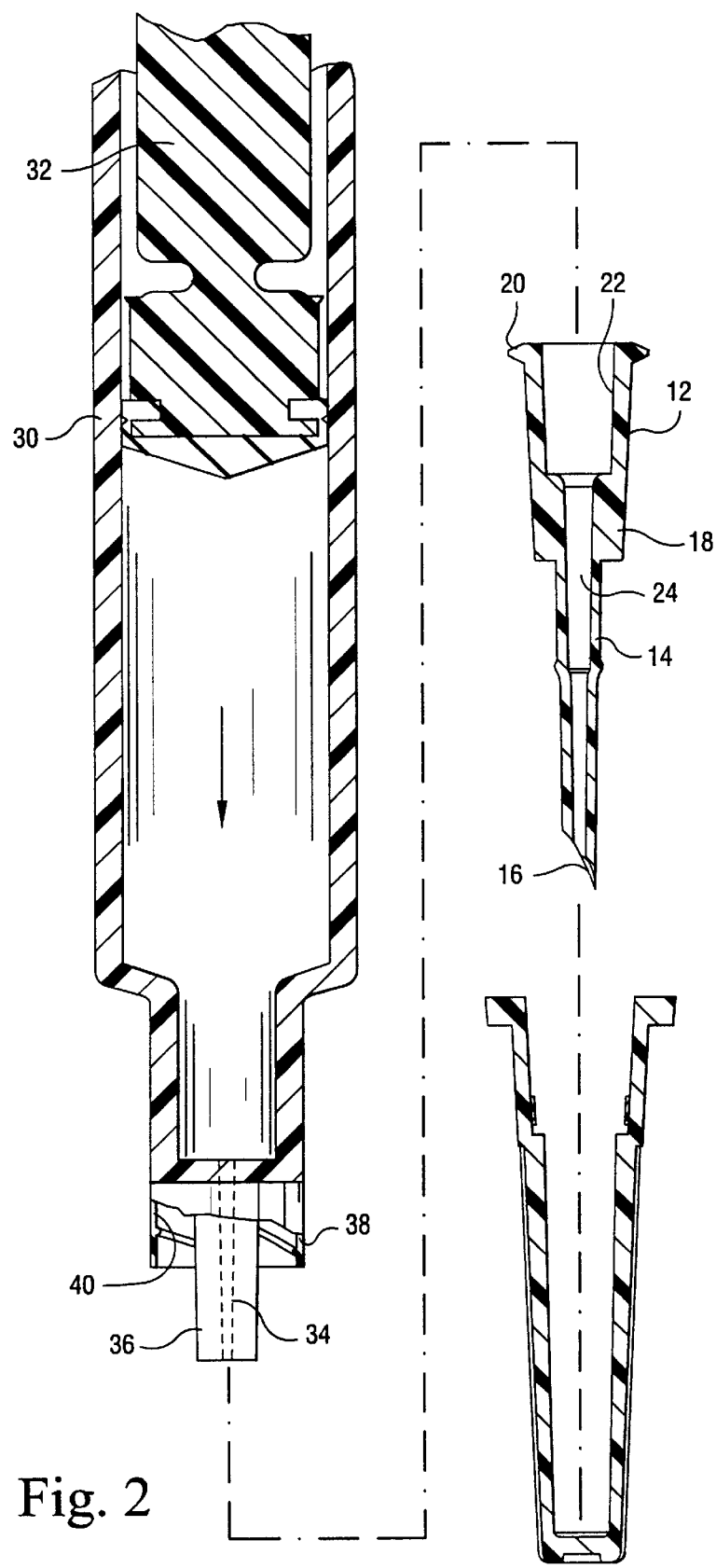
FIG. 2 is a fragmentary exploded cross-sectional view illustrating an end of a syringe barrel, a cannula and cannula guard according to a preferred embodiment of the present invention.

Referring now to the drawings, particularly to FIGS. 1 and 2, there is illustrated a cannula, generally designated 10, formed of plastic material and including a hub 12 and an elongated cannula portion 14 terminating at its distal end at a tapered tip 16 for penetration, for example, through pre-slit or non-pre-slit septums of medication vials. A plurality, preferably four, ribs 18 project radially outwardly from the cannula portion 14 adjacent the base of hub 12. Cannula 10 may be formed of a plastic material such as ABS or polycarbonate. In addition, the hub 12 of the cannula 10 includes a pair of radially projecting flanges 20 at diametrically opposite locations about the proximal end of the cannula 10. As illustrated in FIG. 2, the cannula 10 includes an interior frustoconical section 22 in communication with a bore 24 extending through the cannula portion 14 to the tip 16 of the cannula.

Figure 3:
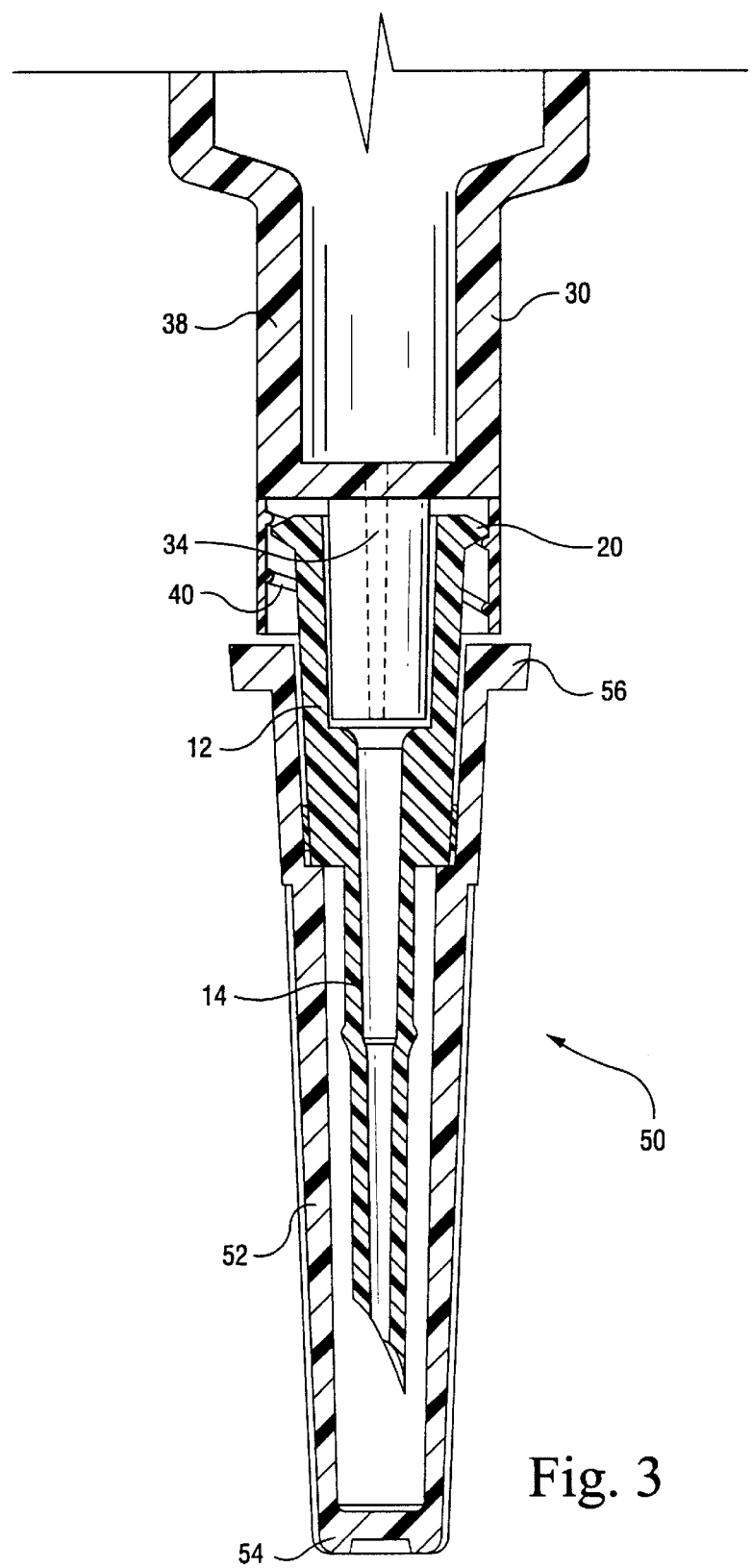
FIG. 3 is a fragmentary cross-sectional view illustrating the cannula guard and cannula assembly attached to the end of the syringe.
Figure 4:
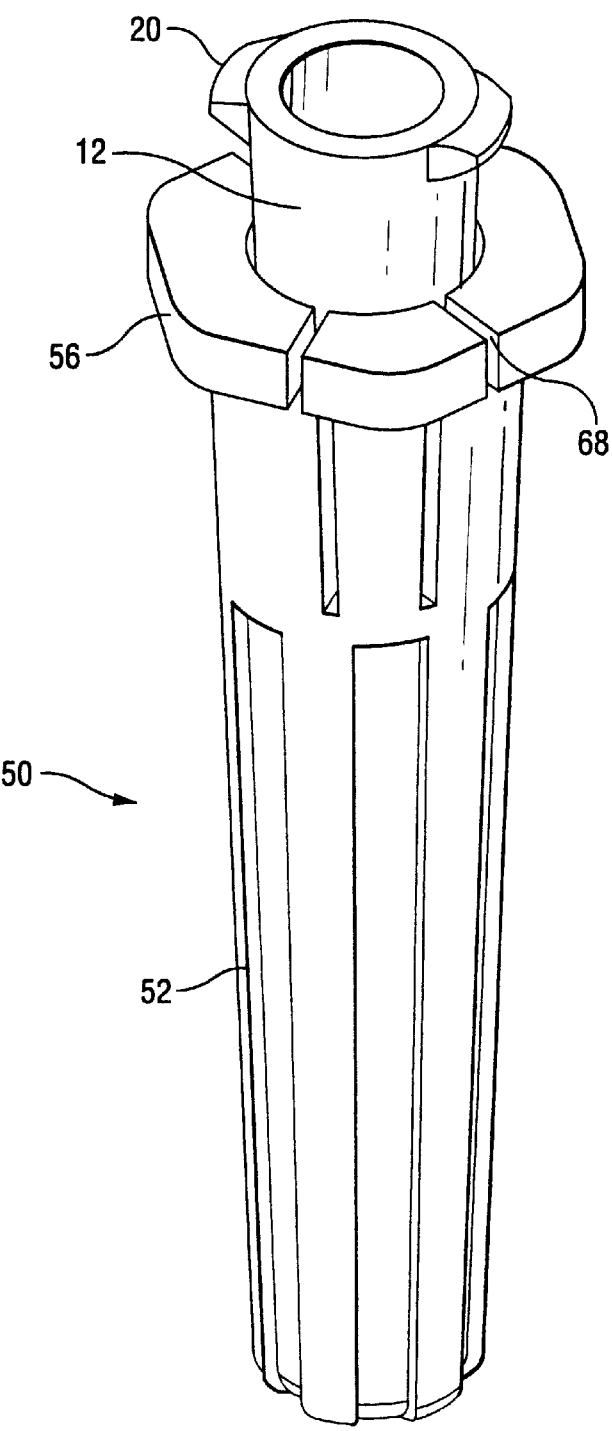
FIG. 4 is a perspective view of the cannula within the cannula guard.
Figure 9:
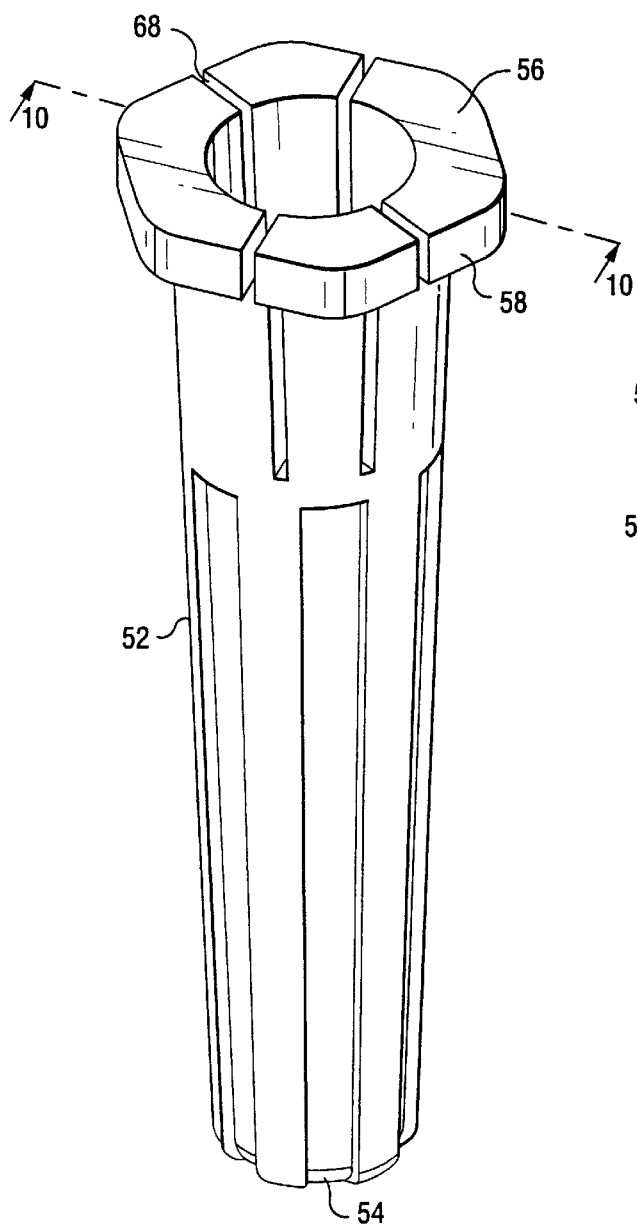
FIG. 9 is a perspective view of a cannula guard.

Referring now to FIGS. 2 and 3, there is also illustrated a syringe comprised of a generally cylindrical syringe barrel 30 having a plunger 32 for facilitating fluid communication into and out of the barrel via an axial extending passageway 34 formed in a frustoconically-shaped projecting tip 36 at the distal end of barrel 30. The tip 36 extends beyond the end of the barrel, which also includes an annular section 38 having female threads 40 along an inside wall surface. It will be appreciated that the hub 12 of the cannula 10 is disposed about the frustoconically-shaped tip 36 such that the axial passage 34 in the barrel lies in communication with the axial passage 24 through the cannula. A Luer lock connection is illustrated in FIG. 3. That is, the frustoconical recess 22 of hub 12 of cannula 10 receives the tip 36 and, upon rotational motion of the cannula 10 relative to the barrel, the flanges 20 engage the threads 40 of the barrel wall 38, securing the cannula to the barrel. It will be appreciated that a fluid-tight communication is formed between the walls of the recess 22 of the hub 12 of cannula 10 and the outer walls of the tip 36.

Referring particularly to FIGS. 5–9, a needle guard, generally designated 50, is provided for overlying the elongated portion 14 of cannula 10 and a part of the hub 12. It will be appreciated that the cannula guard and cannula form a subassembly for not only protecting the cannula but also facilitate application of the cannula to the standard syringe, such as illustrated in FIG. 2. Thus, the cannula guard 50 comprises a generally frustoconically-shaped sleeve 52 closed at its lower end 54 and open at its upper end 56. The upper end of cannula guard 50 also includes a generally radially outwardly extending flange 58. The interior wall surface 60 of the cannula guard 50 is configured for receiving in a tight-fitting friction-fit a portion of the hub 12 of cannula 10. Additionally, the interior surface 60 includes a plurality of radially inwardly directed ramps or projections 62 at circumferentially spaced positions about the wall surface 60. The projections 62 are spaced axially from the open end of the cannula guard 50 a distance such that, upon receiving the cannula within the cannula guard, the projections 62 are axially aligned with the ribs 18 of cannula 10.

Figure 10:
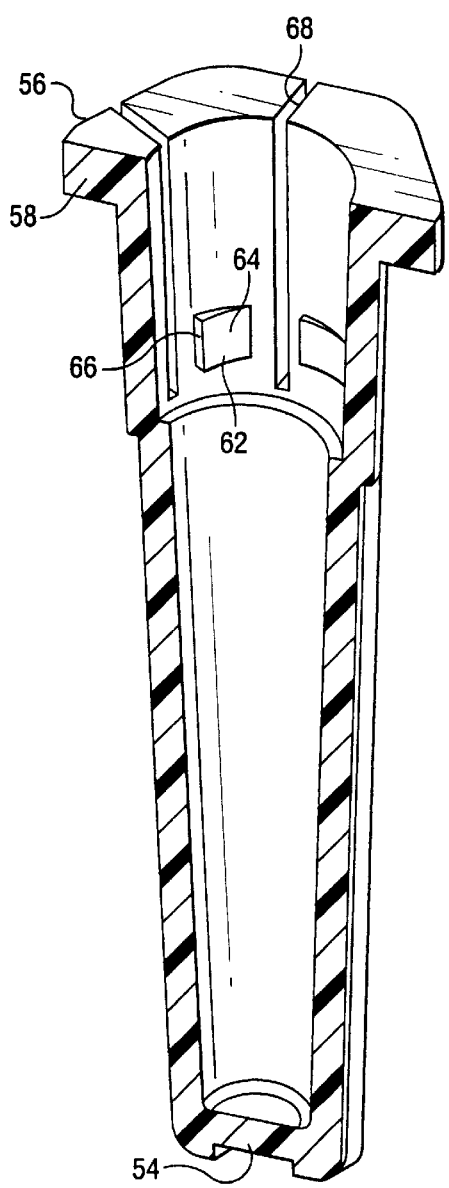
FIG. 10 is a longitudinal cross-section through the cannula guard.

As best illustrated in FIG. 10, the projections 62 have two discrete surfaces. A first surface 64 forms a ramp starting at one end in the wall surface 62 and inclining radially inwardly away from interior surface 60, terminating in a generally radially extending face or stop 66 at the end of the projection 62. A plurality of projections, preferably four, are provided along the interior wall surfaces 62. Additionally, the upper end of the cannula guard 50 has a plurality of axially extending slots, preferably four slots 68. As described below, slots 68 facilitate the application of the cannula guard and cannula assembly to the syringe and the removal of the cannula guard from the cannula without removing the cannula from the syringe.

In use, the cannula 10 and cannula guard are typically provided in an assembled subassembly whereby the cannula can be attached to the distal end of the syringe. To accomplish that, the cannula guard and cannula subassembly are applied to the end of the syringe with the tip 36 of the syringe being received within the recess 22 of the cannula 10. Upon application of the assembly, the assembly is also rotated jointly relative to the syringe. By rotating the assembly, the flanges 20 engage in the threads 40. It will be appreciated that, when the individual grasps and rotates the cannula guard 50, the end stops 66 engage against the sides of the ribs 18 of the cannula. Consequently, a positive rotary torque is applied to the cannula from the cannula guard to thread the flanges 20 about threads 40. Upon tightening the flanges along the threads 40, the cannula guard 50 is removed. To accomplish this, the cannula guard is rotated in an opposite direction and withdrawn in an axial direction relative to the cannula. With such rotation in the opposite direction, the ramps 64 of the projections 62 slip past the outer margins of the ribs 18 of the cannula without applying torque to the cannula sufficient to unthread the flanges 20 from the female threads 40. The slots 68 form flexible leaf portions on which the projections are mounted. Consequently, the plastic material of the cannula guard in the regions of these leaves can flex outwardly when the ramps 64 ratchet past the ribs 18.

Once the cannula guard 50 has been removed, the syringe with cannula attached can be used for its intended purpose, for example, withdrawing medication from a medication vial and ejecting the medication into an intravenous infusion line through an access port with either a pre-slit septum or non-pre-slit septum. It is significant that upon the conclusion of the use of the syringe and cannula 10, that the cannula cannot readily or easily be removed from the syringe using the cannula guard 50. Otherwise, it would be possible for a steel needle to be placed on the tip of the standard syringe after removal of the cannula. Should that occur, a non-safety syringe results, in violation of various state laws mandating use of safety syringes.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. Apparatus for releasably securing a cannula to an end portion of a syringe comprising:

a cannula body having a hub and an elongated cannula portion projecting from said hub terminating in a cannula tip, said body being formed of a plastic material and having a passage therethrough for transmission of a fluid, said cannula hub having a surface for engaging the end portion of the syringe; and a cannula guard including a sleeve closed at one end and open at its opposite end for receiving said elongated cannula portion and a portion of said cannula hub within said sleeve;

said cannula guard and said cannula having cooperable surfaces, respectively, configured to transmit a torque applied to said cannula guard in a first direction to said cannula to engage the cannula and syringe end portion thereby to secure the cannula and syringe to one another and to enable relative rotation of said cannula guard and said cannula without transmission of substantial torque from said cannula guard to said cannula when a torque is applied to said cannula guard in a second direction opposite said first direction.

2. Apparatus according to claim 1 wherein said cannula has an elongated axis, said cannula guard being substantially freely rotatable relative to said cannula in at least one rotational direction about an axis parallel to or coincident with the axis of said elongated cannula portion.

3. Apparatus according to claim 1 wherein said cooperable surfaces comprise ratchet teeth on said cannula guard and radial projections on said cannula engageable with one another in response to the torque applied to said cannula guard in said first direction and relatively movable past one another in response to the torque applied to said cannula guard in said second direction.

4. Apparatus according to claim 1 wherein said cooperable surfaces include a surface carried by said cannula guard movable between a first position spaced from a portion of said cannula and a second position engageable with another of said cooperable surfaces carried by said cannula.

5. Apparatus according to claim 1 wherein said cooperable surfaces include ratchet teeth on said cannula guard and projections on said cannula engageable with one another in response to the torque applied to said cannula guard in said first direction and movable past one another in response to torque applied to said cannula guard in said second direction.

6. Apparatus according to claim 5 wherein said cannula has an elongated axis, said ratchet teeth on said cannula guard and said projections on said cannula lying in generally circumferentially spaced opposition to one another.

7. Apparatus according to claim 1 wherein said cannula guard and said cannula have a first pair of cooperable surfaces respectively engageable with one another for enabling a force applied to said cannula guard in a first axial direction to be transmitted to said cannula for securing said cannula hub and the end portion of the syringe to one another and a second pair of cooperable surfaces on said cannula and said cannula guard, respectively, and engageable with one another for enabling a force applied to said cannula guard in a second axial direction opposite said first axial direction to be transmitted to said cannula hub for removing said cannula hub from the end portion of the syringe.

8. Apparatus according to claim 1 in combination with a syringe having an axially elongated barrel for containing a fluid and terminating in an annular projection at a distal end having female threads, said cannula hub having a pair of radial flanges for threading engagement with the female threads on said annular projection.

* * * * *